United States Patent [19]

Bonsignore

[11] Patent Number: 5,470,944
[45] Date of Patent: Nov. 28, 1995

[54] PRODUCTION OF HIGH MOLECULAR WEIGHT POLYLACTIC ACID

[75] Inventor: Patrick V. Bonsignore, Joilet, Ill.

[73] Assignee: ARCH Development Corporation, Chicago, Ill.

[21] Appl. No.: 835,166

[22] Filed: Feb. 13, 1992

[51] Int. Cl.$^6$ ..................................................... C08G 63/08
[52] U.S. Cl. ...................... 528/354; 424/78.06; 424/423; 525/415; 525/450; 528/361
[58] Field of Search .................................... 525/450, 415; 528/354, 361; 424/78, 78.06, 423

[56] References Cited

U.S. PATENT DOCUMENTS 3,476,712  11/1969  Fukui et al. .
4,826,945  5/1989  Cohn et al. ................................ 528/76
4,999,417  3/1991  Domb ....................................... 528/271
5,110,852  5/1992  Gogolewski et al. ................... 525/450

FOREIGN PATENT DOCUMENTS 1426409  9/1974  United Kingdom .

OTHER PUBLICATIONS

"Preparative Methods of Polymer Chemistry", Sorenson et al., Interscience Publishers, Inc., pp. 132–147 Mar./(1961).
"Permeability and Other Film Properties of Plastics and Elastomers", p. 4 Jun./(1994).
"Polymerization of Bis(2–Oxazoline) Compounds with Dicarboxylic Acids", Yasuo Sano, *J. Polymer Science: Part A: Polymer Chemistry*, vol. 27, 2749–2760 Nov./(1989).
"Preparation of a Crystalline Poly(Ester–Amide) by the Polyaddition Reaction of Bisoxazoline and a Dicarboxylic Acid", *Polymer Letters*, vol. 4, pp. 257–260 Apr./(1966).
"2–Oxazoline für die reaktive Extrusion", Birnbrich, et al., *Kunststoffe* 83 Feb./(1993).
"Chain Extenders for Polyesters. I. Addition–Type Chain Extenders Reactive with Carboxyl End Groups of Polyesters", Inata, et al., *Journal of Applied Polymer Science*, vol. 30, 3325–3337 Apr./(1985).
"Biodegradable Plastics and Polymers", Doi, et al., Jan./1994 Elsevier Science B.V.

*Primary Examiner*—Shelley A. Dodson
*Attorney, Agent, or Firm*—Reinhart, Boerner, Van Deuren, Norris & Rieselbach

[57]  ABSTRACT

A degradable high molecular weight poly(lactic acid). A poly(lactic acid) has a terminal end group of one of carboxyl or hydroxyl groups with low molecular weight poly(lactic acid) units coupled with linking agents of di-isocyanates, bis-epoxides, bis-oxazolines and bis-ortho esters. The resulting high molecular weight poly(lactic acid) can be used for applications taking advantage of the improved physical properties.

13 Claims, No Drawings

PRODUCTION OF HIGH MOLECULAR WEIGHT POLYLACTIC ACID

The United States Government has rights in this invention pursuant to Contract No. W-31-109-ENG-38 between the U.S. Department of Energy and The University of Chicago, representing Argonne National Laboratory.

BACKGROUND OF THE INVENTION

The invention relates generally to the production of modified polymers of high molecular weight poly(lactic acid) useful for waste disposal or for agricultural purposes. More particularly, the invention relates to producing high molecular weight poly(lactic acid) by coupling lower molecular weight version of the polymer (molecular weight of about 2,000–15,000) by various coupling agents. These increased molecular weight products have improved mechanical properties while still degrading in an environmentally safe manner. The modified polymers and polymer blends are also usable for garbage bags or other waste disposal purposes and can be incinerated since upon burning only environmentally safe materials are produced. It is now recognized that many plastic materials useful for packaging as well as waste disposal present serious environmental problems because they either do not degrade in landfills or produce toxic components upon incineration. More attention has been devoted to environmentally safe plastic materials, particularly since Congressional hearings have determined that over 135 thousand metric tons per year of plastic is discarded at sea alone with some 639,000 plastic containers and bags tossed into the ocean every day. In addition to this intolerable situation, the amount of nondegradable plastic materials used for packaging as well as garbage disposal has caused landfill areas (previously thought to be entirely adequate for urban disposal sites) to become filled and unusable. Waste disposal has become a very serious problem in this country as well as world-wide.

Accordingly, there is a need to provide plastic materials suitable for packaging and waste disposal which at the same time will also be degradable to products which are environmentally safe. However, it is also generally recognized that higher molecular weights (above at least 25,000) are needed for poly(lactic acids) to have good physical properties.

In the area of medical applications, the polymers of lactic acid and glycolic acid achieved their first commercial success as fiber materials used for reabsorbable sutures. These were first announced by Davis & Geck in 1969 and since then have significantly displaced collagen as resorbable sutures. The polymers of lactic acid are well suited for other prosthetic devices because they are hydrolyrically degradable, biocompatible, and also they are thermoplastics suitable for the extrusion, molding, etc., of cross-sectional designs.

Kulkarni first proposed the use of poly(d,l-lactic acid) as a resorbable prosthetic device. Working in the U.S. Army's Biomedical Laboratory, Kulkarni recognized the possibilities of this material for repair and reconstruction of traumatic wounds. The materials replace steel plates, pins, etc., allowing the bone to remodel its stresses naturally as the polyesters gradually resorb. A second operation to remove the metal device is obviated as is the need for a second surgical procedure with the use of conventional, autogenous grafts. Subsequent work at the U.S. Army Institute of Dental Research again demonstrated biodegradability and biocompatibility, in this case of implants or more sizable cross-sections such as films, slabs, and pins that were not oriented, plasticized (as with sutures) and for copolymer compositions that also included d,l-lactic acid. The polymers of lactic acid then act as a temporary fastnet and scaffold for hard or soft tissue, providing strength until natural healing occurs.

Since this beginning in the medical field, a number of research organizations have worked extensively on resorbable prosthetic devices. Mandibular fractures, long bone internal fixation, osteogenesis, nerve regeneration, vascular prostheses, and Achilles tendon repair are just a few examples illustrating the variety of devices. A number of these devices are just now beginning to emerge from pre-clinical and clinical trials.

There are probably only a few ten thousands pounds of poly(lactic acid) marketable for prosthetic devices. Based on the small weights involved, the expense is quite large to produce premium purity poly(lactic acid) products using current methods of condensation polymerization of free acids and catalytic, ring opening polymerization.

The use of the polymer in these medical devices may draw attention to these degradable plastics for larger uses. Assuming 400,000 metric tons of pesticide are used per year in the U.S., a sizable use of poly(lactic acid) as controlled release coatings is possible. This application would require 2–3 times the tonnage of the formulation agent, poly(lactic acid). Success in this market may depend on government regulations to prevent pesticide runoff or producers successfully pursuing controlled release advantages. With only a modest market penetration the use for pesticide and diverting agents could reach a few tens of million pounds consumption per year.

The benefits to the corn grower could be substantial. An acre of land devoted to corn can be expected to yield 100 to 140 bushels, depending on weather and agricultural practices. The yield can be expressed in terms of lactic acid that could be generated from corn starch with a good fermentation system. Because the fermentation of glucose to lactic acid involves no loss of carbon dioxide, lactic acid production could be 4,000 to 5,000 pounds per acre.

This output should be contrasted with the potential for making ethanol. About 2.4 gallons of ethanol per bushel is the limit on ethanol production because about half of the weight of glucose is lost as carbon dioxide. Therefore, about 240 to 340 gallons of ethanol can be made from the corn available from an acre of land. Processes that produce carbon dioxide as a by-product are also less desirable because of increasing concern about its accumulation in the atmosphere as a "Greenhouse Gas."

At a selling price of $1.50 per gallon, an acre of land would yield $360 to $500 of ethanol. The same acre would yield $1,000 to $1,250 of lactic acid with a fermentation of comparable difficulty and by-product feeds of comparable value. The impact of lactic acid production on corn grower prosperity would, however, depend on market size and the development of large-scale markets. The fuel market for ethanol is already developed but is shaky from the viewpoint of near-term economic driving force. Building a lactic acid commercial foundation for future prosperity could have substantial returns for corn growers.

Recently, it has been determined that high carbohydrate food waste presently produced in the United States as cheese whey permeate and in conjunction with potato processing facilities is convertible in an environmentally benign process to provide a feed stream for lactic acid. Lactic acid is desirable because it is a naturally occurring compound which degrades to environmentally safe products. In addition, it has been discovered that oligomers of poly(lactic acid) are useful as plant growth promoters, see U.S. Pat. No. 4,813,997 issued to Kinnersley et. al. With the discovery of the conversion of high carbohydrate food waste to feedstocks for lactic acid, it has become feasible through the present invention to formulate various copolymers and blends of poly(lactic acid) for a wide range of agricultural and packaging uses. These applications meet all the objectives set forth above and provide environmentally safe materials to replace presently used plastics that are difficult to dispose of in a safe manner.

Accordingly, it is an object of the invention to provide a novel degradable high molecular weight polymer of modified poly(lactic acid) polymers or blends thereof.

Another object of the invention is to provide an improved poly(lactic acid) polymer and copolymer of high molecular weight by coupling lower molecular weight units using difunctional coupling agents.

It is a further object of the invention to provide a novel high molecular weight, modified poly(lactic acid) polymer using a hydroxyl group or carboxylic acid terminated poly(lactic acid) polymer and using a coupling agent selected from the class consisting of di-isocyanates, bis-epoxides, bis-oxazolines and bis-ortho esters.

A still further object of the invention is to provide an improved high molecular weight poly(lactic acid) polymer comprising a co-polymer of the high molecular weight poly(lactic acid) and a modifying monomer selected from the class consisting of p-dioxanone present in an amount up to about 20% by weight, 1,5 dioxepan-2-one present in an amount up to about 20% by weight, and 1,4 oxathialan-2-one, 4,4 dioxide present in an amount up to about 20% by weight, or mixtures thereof, the modifying monomer being present in an amount not greater than about 20% by weight.

An additional object of the invention is to provide a novel method and new poly(lactic acid) polymer having terminal mercaptan groups readily oxidizable to di-sulfides.

The invention consists of certain novel features and a combination of parts hereinafter fully described, and particularly pointed out in the appended claims, it being understood that various changes in the details may be made without departing from the spirit, or sacrificing any of the advantages of the present invention.

DETAILED DESCRIPTION OF THE INVENTION

Polymers and copolymers of lactic acid (hereinafter "PLA") are transparent, colorless thermoplastics with a wide range of physical properties that mimic those of some conventional thermoplastics. When exposed to moisture or biological fluids, these modified PLA plastics hydrolyze slowly over a period of several months to natural, harmless materials such as lactic acid. The copolymers of lactic acid and glycolic acid were originally developed and marketed as an industrial product as resorbable sutures. These PLA polymers and copolymers have high strength and biocompatibility and have controlled degradability although prior art methods are extremely expensive to implement in producing the PLA.

Poly(lactic acid) (PLA) and poly(glycolic acid) are conventionally prepared by either condensation polymerization of the free acids or by catalytic, ring-opening polymerization of the dilactones. Both PLA and poly(glycolic acid) are environmentally compatible because they degrade respectively to lactic acid and glycolic acid, both natural harmless products. While these polymers degrade primarily by hydrolysis, with the addition of certain other materials they may degrade also by exposure to sunlight or any other source of UV light. Upon incineration, the polymers burn with a clean blue flame, rather than giving off poisonous or corrosive gases as some plastics do.

The fact that the thermoplastics based on PLA degrade slowly over a period of several weeks up to about one year leads to another important advantage of relatively good shelf life. Compared to water-soluble or water-swelled polymers, which fall apart quickly in water, the modified PLA polymers can be classified as moisture sensitive because they degrade slowly. For instance, after a month's immersion in water, PLA and certain of the copolymers thereof show no degradation of the molecular weight. But after six months' immersion in water, physical properties drop significantly. For instance, water degradable modified PLA copolymers may be made from monomers of lactic acid and modifying monomers selected from the class consisting of ethylene-and polyethylene-glycols, propylene-and polypropylene-glycols, p-dioxanone, 1,5 dioxepan-2-one, 1,4-oxathialan-2-one, 4,4-dioxide and various mixtures thereof. The physical properties such as crystallinity, melting point, degradation rate, elasticity and the like can be varied depending upon the amount and the type of copolymer formed.

L(+) or D(-) PLA have a crystallinity of about 37%, which crystalline portion melts at about 175° C., while the amorphous portion has a glass transition temperature of about 53° C. Racemic poly(lactic acid) is amorphous and has no crystalline melting point but softens or has a stick point of about 50°–75° C. depending on molecular weight. The crystallinity of poly (glycolic acid) is about 52% with a crystalline melting point of about 230° C. Copolymers of L(+) lactic and glycolic acid drop in crystallinity as the composition moves away from either pure constituent and disappears in the range of 25% to 75% L(+) lactic acid.

The elasticity of the material will vary from glassy materials which are relatively nonelastic to high-modulus elastic materials. The degradation rates will vary from intermediate, to fast, to very slow, to none depending upon the amounts of PLA or poly(glycolic acid) utilized.

In general, the various physical attributes discussed above can be varied among a wide range of physical properties depending upon the types and amounts of copolymers used for the final material. Depending upon the end usage desired, the modifying polymer for the PLA is preferably present in the range from about 5% by weight to about 40% by weight so as to provide a water degradable modified PLA copolymer which has suitable physical properties for the end use selected.

It is contemplated that the various copolymers of PLA may be useful for a variety of medical, agricultural and waste management uses (see discussion hereinbefore). In a particular example, the copolymers may be used as coatings on or as matrices for seeds, seedlings, pesticides, herbicides, fertilizers and mixtures thereof, wherein the coating or matrices provide a controlled release of the coated or embedded material depending upon the thickness of the coating or percent of active ingredient embedded in the matrix. The coatings may have a thickness in the range of from about 0.25 microns to about 4 microns, so that release rates can be varied as required. The active ingredients, such as seeds, pesticides, herbicides, fertilizers or mixtures thereof also may be mixed with the copolymer and extruded as pellets, with the active ingredient dispersed in a matrix of the copolymer. Here, the release of active ingredients will be controlled by varying the type of copolymer and the amount thereof present. It is preferred that where the copolymer is used as a matrix for an active ingredient, it is present in the range of from about 2% to about 40% by weight, that is, the active ingredient is present in the range of from about 60% to about 98%. Accordingly, it is seen that fertilizers, for instance such as urea or other nitrogen rich fertilizers, can be coated with various thicknesses of coating or dispersed in a matrix to provide a continuing release of the coated or dispersed materials over a wide range of time so as to prevent crop burning and other undesirable side effects when too much urea or other fertilizer is released at any one time.

In general, the copolymers of PLA are useful with molecular weights in a range of at least about 20,000 to about 100,000 for the uses aforesaid as coatings or matrices. Where sheet materials are desired, such as in agricultural mulch films and the like, molecular weights of greater than about 25,000 are preferred and in particular, molecular weights in the range of at least about 25,000 to 100,000 are preferred for agricultural mulch films which upon time and exposure to moisture and UV light will degrade to the constituent lactic acid and other monomers.

The copolymer, particularly for agricultural use will often be present as a matrix or as a coating for the active material. As described hereinbefore, PLA has been used as an encapsulator in the medical field. For example it has been used for preparation of encapsulated active materials with PLA coatings (see, Ogawa et. al. in a paper entitled New Technique to Efficiently Entrap Leuproside Acetate into Microcapsules of Polyiacticacid or Copoly (Lactic/Glycolic) Acid in Chem. Pharm. Bull. 36(3) 1095–1103 (1988)). Further, a process of preparing microcapsules of lactides or lactide copolymers has been patented by Gardner, Jan. 20, 1987, U.S. Pat. No. 4,637,905, the disclosure of which is incorporated herein by reference. Similarly, and also in the pharmaceutical field, microencapsulation has been taught by Lapka et. al. U.S. Pat. No. 4,622,244, issued Nov. 11, 1986, the disclosure of which is incorporated herein by reference.

The various modifying monomers which form the new copolymers hereinbefore disclosed, provide a wide range of physical properties from highly crystalline to amorphous materials thereby providing controlled degradation rates upon exposure to either UV light or to moisture or to both.

While Sinclair in an article entitled Slow-Release Pesticide System. Polymers Of Lactic and Glycolic Acids as Ecogolically Beneficial, Cost-Effective Encapsulating Materials, teaches the use of combinations of polymers of glycolic and lactic acids as a matrix for a pesticide, Sinclair does not show or suggest the use of the modified copolymers of PLA nor high molecular weights. Specifically, the polypropylene glycol and polyethylene glycol used as modifiers are a different class of materials from the glycolic acid taught by Sinclair.

The present invention permits preparation of a copolymer of superior properties and can be used in demanding applications as well as to control the release rate of the active material to the environment. Where the active material is a high urea content fertilizer, the controlled degradation of the matrix permits the urea to be released at a rate which prevents crop burning and other undesirable side effects. Where the active material is a herbicide or pesticide, the controlled degradation of the matrix permits continual application of the pesticide or herbicide over a prolonged period of time, thereby permitting fewer applications by the farmer and ultimately, releasing less of the active material into the environment since only so much as needed is added at any one time.

It can be seen therefore that increased savings are available to the farmer, both due to fewer applications as well as to administering less of the active material overall. Another added feature and benefit of the present invention is the use of modified PLA as matrices or coatings for seeds or seedlings which when germinating or growing are provided with a concentration of growth promoting oligomers of PLA or the disclosed copolymers as the modified PLA copolymer degrades in situ. Whenever the disclosed copolymers degrade in an agricultural site, there will be a variety of oligomers of PLA and copolymers thereof present in a wide variety of chain lengths or molecular weights. Some of these materials are proven growth promoters.

Both agricultural and waste disposal uses require plastic materials for a wide variety of products including, inter alia, agricultural mulch films, compost and garbage bags, which, depending on the polymers selected, degrade over a wide range of time. For instance, an agricultural mulch film may be designed to degrade from a few days to a few months. While a plastic garbage bag certainly will not be designed to degrade over a few days.

Further, when used as a film for trash bags and the like, the film can be designed so as to degrade without the presence of UV light such as in conditions which occur in landfills. High Molecular Weight Poly(lactic acid)

High molecular weight (hereinafter "HMW") PLA (e.g., above at least about 25,000 and preferably above 50,000–100,000) has substantially improved physical properties and is useful in self-supporting films and other applications demanding improved properties over conventional PLA. This need has existed since the early work of Carother's in the 1940's concluded that HMW-PLA could not be economically produced; and this condition still exists at this time. The known method of catalytic, ring opening polymerization of lactides is an extremely inefficient method requiring implementation at high temperature and is time consuming relative to the invention of the Applicant which has solved this long standing problem.

The method of the Applicant concerns a low temperature chemical reaction to make HMW-PLA. In this method selected difunctional linking agents can be used in small quantities to produce the HMW-PLA without substantially affecting the properties of the intrinsic HMW-PLA.

The linking agents of the invention interact with the terminal groups of the PLA. These terminal groups in self condensed lactic acid form ester linkages by splitting out water molecules. The result is an end hydroxyl group (OH) and an end carboxylic acid group (COOH). Generally, linking agents usually operate effectively with either the hydroxyl or carboxylic acid end groups. The kinetic reaction rates of the linking agent with the two different groups will likely be different. The starting PLA units can be modified in a known manner to produce a PLA batch containing either all hydroxyl or all carboxylic acid end group. For example, PLA can be prepared by self condensing lactic acid in the presence of a glycol or other suitable molecular species with a hydroxyl group at both ends. Polyester chain growth will be biased toward molecular species having a hydroxyl end group. Another method to produce hydroxyl terminal groups is to prepare conventional low molecular weight PLA and post react the carboxylic acid end group with an epoxide to convert it to a hydroxyl end group.

In order to obtain a PLA starting batch with solely carboxyl end groups, the same general principles also apply as described above for hydroxyl end groups. For example, one can prepare the low molecular weight PLA by self condensing lactic acid in the presence of a dicarboxylic acid, such as a succinic-acid or adipic acid. Polyester chain growth will be biased toward PLA having carboxylic acid end groups. In the other case, the PLA can be post reacted such that the hydroxyl end groups react with a cylic dicarboxylic acid anhydride to convert to carboxylic acid end groups.

Coupling of the low molecular PLA in the starting batches can be accomplished using the isocyanate group. This group is highly reactive, readily adding active hydrogen compounds, such as hydroxyl and amine groups across its nitrogen/carbon double bond. An alcohol (R-OH) will readily add to an isocyanate (R-N=C=O) to form a coupled product.

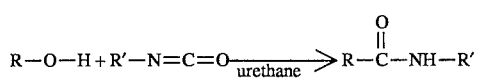

If the above reaction is difunctionalized with respect to both hydroxyl ended molecular species such as PLA (with both ends derivatized as hydroxyl groups) and with respect to isocyanate ended species, e.g., di-isocyanates such as MDI (methylene-bis-phenylisocyanate) and HDI (hexamethylene di-isocyanate), the resultant polyester will be the desired HMW modified PLA containing urethane linkages.

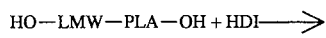

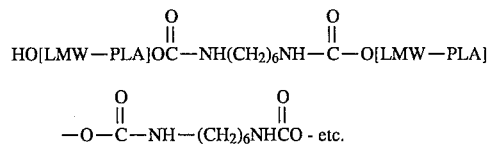

The reaction of an isocyanate group with a carboxylic acid group is more complex and slower than with hydroxyl groups, but a stable linkage can be formed. The reaction proceeds in two stages with the formation first of an unstable carbamic acid anhydride which then spontaneously decomposes with release of carbon dioxide and final formation of a stable amide linkage.

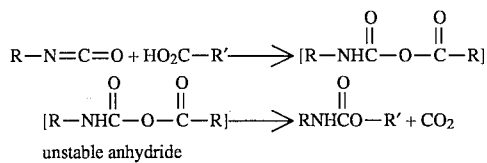

Here too, difunctionalization of the reaction of a di-isocyanate with a polymer chain ending in a carboxylic acid group can form a coupled polymeric chain by the mechanism shown above. (NCO) Di-isocyanate Capped Prepolymer In the example given above the HMW PLA is produced by mixing together a 1:1 ratio of reactive segment to di-isocyanate

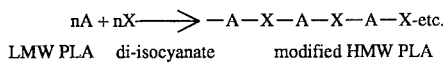

An activated functionalized LMW PLA can be formed by reacting a LMW PLA with two moles of a di-isocyanate (X) such as HDI,

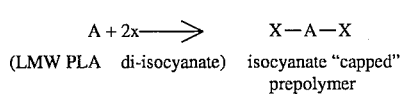

Note that the capped prepolymer is not yet a high molecular weight PLA. It can be converted to modified HMW PLA by post reaction with a variety of techniques.

If one mole of X-A-X is reacted with one mole of A, the end result will be the same as discussed in the previous section.

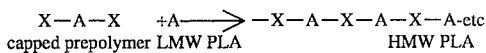

If instead of one mole of X-A-X reacting with one mole of A, the second "A" mole is a blend of A with other difunctional "A"-like species (with the total molarity being 1), e.g., 80% A and 20% B, then a modified-modified HMW PLA will result in which the "B" functionality could impart alternate physical property attributes to the final modified HMW PLA. Some possibilities for the "B" component are:

PPG; polypropylene glycol, of varying molecular weight to give a softening or plasticizing effect;

PEG; polyethylene glycol, of varying molecular weight, to give a softening effect attendant with significantly increased hydrophilicity or water sensitivity for enhanced susceptibility to hydrolyric degradation;

DHES; bis-hydroxyethyl sulfone, HO-CH$_2$CH$_2$SO$_2$-CH$_2$-OH, whose incorporation in the modified HMW PLA would introduce the photolyticaly labile - SO$_2$ - function, thereby imparting photodegradability to the HMW PLA.

An alternate approach to the conversion of isocyanate capped LMW PLA to high polymer is the water coupling of two isocyanate functions. Again a two step reaction is involved. The first mole of isocyanate reacts with water to form an unstable carbamic acid. Spontaneous decomposition of the carbamic acid occurs with release of carbon dioxide and formation of a primary amine. A second molecule of isocyanate then readily reacts with the amine to form a urea bridge between the original two isocyanate molecules:

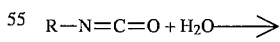

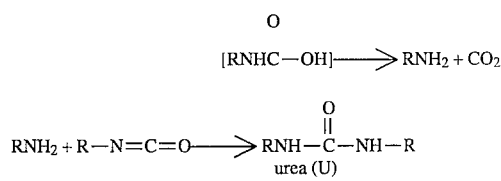

The reaction of the isocyanate capped LMW PLA with water can lead to a HMW PLA bridged with urea (U) groupings:

The chemistry of isocyanate reactivity with hydroxyl groups presages a potentially attractive approach to the treatment of paperboard stock with PLA coatings. That is, if an isocyanate capped LMW PLA prepolymer were used to saturate a cellulosic (paperboard) substrate, the terminal isocyanate groups will effectively bond to cellulosic hydroxyl groups.

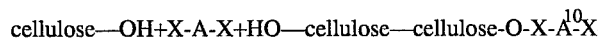

The net effect of the above treatment would be a cellulosic substrate with PLA polyester segments chemically bonded throughout the matrix. The crosslinking effect of these PLA bridges enhance the physical properties of the final coated paperboard stock. The hydrolytic degradability of the PLA segments should be retained.

In the preferred form of this invention, due to the high reactivity of isocyanate groups with active hydrogen compounds, one should preferably avoid excess isocyanate functionality. Excess isocyanate, over that required to form the coupled PLA, can eventually lead to crosslinking and insolubilization of the desired linear, soluble and thermoplastic chain extended PLA. Three dimensional crosslinked networks of PLA can lead to diminished processibility by standard plastic processing techniques such as melt extrusion of films or solvent casting of films. Strict adherence of reaction conditions to guarantee equimolar ratios of hydroxyl to isocyanate groups is preferable to guarantee processability for the di-isocyanate coupled HMW PLA.

Bis-epoxides can be used as coupling agents for PLA. One example is Shell Chemical Company's EPON® 828 which is used in the formation of epoxy resins.

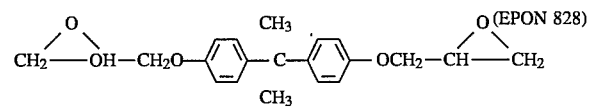

Epoxides $CH_2$-CH-R readily react with active hydrogen compounds to form bridged compounds. For example, hydroxyl groups readily add across epoxide functions to give coupled products:

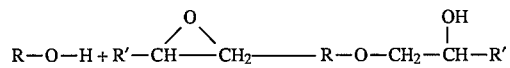

Reaction of hydroxyl terminated LMW PLA with a bis-epoxide, such as EPON 828, provides a linear chain extended PLA high polymer. In the above indicated coupling reaction, crosslinking insolubilization could occur if greater than equivalent ratio of bis-epoxide to reactive hydroxyl or carboxyl group is used. This insolubilization could result from participation of the newly formed hydroxyl group which results when the epoxide ring reacts. Fortunately the newly generated hydroxyl group is much less reactive since it is an internal secondary hydroxyl group and is sterically hindered by the bulky adjacent aromatic rings.

Epoxides react cleanly and vigorously with carboxylic acid groups to form coupled products (ester linkages)

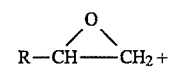

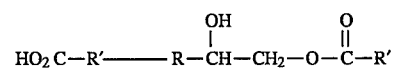

Carboxylic acid terminated LMW PLA react more rapidly with epoxide functions than hydroxyl groups so that chain coupling is relatively clean.

Oxidative Coupling of Mercaptan Terminated PLA (SH)

Mercaptan groups (-SH) are readily oxidized to disulfides by the reaction,

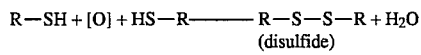

If LMW PLA could be functionalized to end in mercaptan groups then mild oxidation conditions leads to modified HMW PLA containing disulfide bridges.

One approach to mercaptan termination of PLA is by the mercaptoethylation of terminal hydroxyl groups of PLA with ethylene episulfide (also named "thiirane"). Generic Reaction:

Specific Reaction:

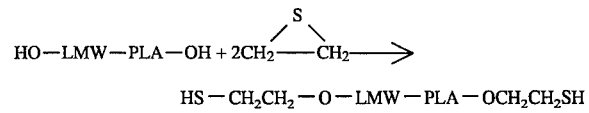

Oxidative Coupling Reaction:
HS-LMW-PLA-SH+[O]→
-[LMW-PLA]-S-S-[LMW-PLA]-S-S etc The mercaptan capped PLA prepolymer ("MCP") should have many of the desirable attributes of the isocyanate capped PLA prepolymer (ICP), especially having low handling viscosity. In contrast to the indiscriminate reactivity of ICP with any and all active hydrogen species (hydroxyl, amine, carboxylic acids) for curing to HMW or inactive species, MCP "curing" to HMW will be selectively limited to oxidative curing conditions. For some coating applications a crosslinked thermoset coating can be desirable, e.g., for paperboard coating perhaps to slow down the rate of hydrolyric degradation. To introduce crosslinking into the cured coating, multifunctional mercaptans can be added to the MCP before subjecting to oxidative coupling.

Regarding specific oxidation technology for converting HS-PLA-SH to HMW PLA, an especially attractive approach is available in the use of dimethyl sulfoxide ("DMSO") with $CH_3$-SO-$CH_3$ as an oxidative functional reaction solvent: 2RSH+$CH_3$-SO-$CH_3$-R-S-S-R +$CH_3$-S-$CH_3$+$H_2O$ While there has been disclosed what is considered to be the preferred embodiment of the present invention, it is understood that various changes in the details may be made without departing from the spirit, or sacrificing any of the advantages of the present invention.

EXAMPLE 1

Isocyanate Coupled PLA

A low molecular weight poly(lactic acid) (PLA) of 68/32 ratio of L(+)/D(−) was prepared by the direct self condensation of a lactic acid mixture of 285g of Natural (97+% L(+)) lactic acid from PURAC-USA and 425g of racemic lactic acid. The self catalyzed condensation was carried out at atmospheric pressure with removal of water of solution and reaction with xylene as the azeotroping non-solvent. Over a 16 hour reaction time the temperature rose to 170° C. Partial distillation of xylene allowed the temperature to rise to 190° C. where it was held for an additional 18 hours. The xylene solvent was stripped off under vacuum and the molten PLA poured into a metal pan to cool and solidify. The number average molecular weight (MWn) determined by carboxylic acid end group titration (NaOH in benzyl alcohol) was 2550, i.e., a degree of polymerization (DP) of ca 35.

Before chain coupling, $C_2O$ H end groups were converted to hydroxyl groups by reaction with butyl glycidyl ether (BGE). To 500g (0.196 mole) of the 2550 MW PLA held at 100°–110° C. was added 26g (0.20mole) of BGE and 0.5g of a tertiary amine catalyst (Airco Polycat 17). After 30 minutes reaction at 110° C. the temperature was raised to 150° C. for an additional 30 minutes. The hydroxyl terminated PLA, on cooling, showed a significantly lowered, but not completely eliminated carboxylic acid content, i.e., less than 10% of its original value.

To 45.1g of the hydroxyl terminated PLA polyester (0.017 mole) dissolved in 50 ml of dry acetone was added 4.5g (0.018 mole) of MDI (methylene bis-phenylisocyanate). No change in viscosity was noted until 5 drops of stannous octoate catalyst was added. Over a two hour reaction period (room temperature) the viscosity of the solution increased significantly. The solution was poured onto a glass plate and allowed to evaporate to dryness overnight.

After overnight drying, a strong, coherent, glass-clear, somewhat rubbery film could be stripped from the glass plate. This tough film is in marked contrast to the base 2550 MW PLA which is incapable of forming a self supporting film at this MW.

EXAMPLE 2

Isocyanate Coupled Block Copolymer of PLA with PPG

To 12.4g ($4.6 \times 10^{-3}$ mole) of the hydroxyl terminated PLA of example 1 and 4.6g ($4.6 \times 10^{-3}$ mole) of polypropylene glycol, Union Carbide's PPG 1025, MW 1000, dissolved in toluene (ca 50 ml) was added 2.3g ($9.2 \times 10^{-3}$ mole) of MDI dissolved in toluene/acetone (1/1). To this solution was added about 0.2g of stannous octoate catalyst. The solution was allowed to react overnight at room temperature and then poured out onto a glass plate to evaporate solvents.

After one week, the resultant film, on removal from the glass plate was found to be glass clear, very tough and elastomeric. This film was thermoplastic in nature since it could be repeatedly melt pressed in a Carver Press (platen temperatures 200°–230° F.). It was also easily soluble in acetone.

A comparable blend of PLA and PPG without the MDI coupling agent, solvent cast onto a glass plate, did not lead to a coherent self-supporting film.

EXAMPLE 3

Prepolymer Approach to Block Copolymer of PLA with PPG

As isocyanate capped LMW PLA prepolymer was prepared by reacting two moles of hexamethylene-diisocyanate (HDI) with one mole of PLA:

A solution of 93.7g (0,025 mole) of PLA, MW 3750, and 8.4g of HDI (0,050 mole) in toluene (ca 50 ml) was allowed to react at room temperature for seven days with rigorous exclusion of water vapor. A moderately viscous slightly hazy solution resulted.

Reaction of 15.2g of this NCO capped PLA prepolymer solution (0.0025 mole capped PLA) with 2.5g (0.0025 mole) of PPG 1025 (MW 1000), catalyzed with 5 drops of stannous octoate, at 100°–120° C. for 20 minutes gave a tough rubbery mass. This catalyzed mix could be melt pressed to tough glass clear, rubbery and elastic film, very similar in physical properties to the film realized in example 2.

Isolation and pressing of the prepolymer without the added PPG co-reactant also yielded a film, but this film was extremely soft and stretchable with no elastic memory and very little tear strength.

What is claimed is:

1. A poly(lactic acid) having an average number molecular weight of about 25,000–100,000, comprising:

poly(lactic acid) polymeric units having terminal end groups selected from the group consisting of one of carboxyl and hydroxyl groups, said polymeric units coupled one to another by coupling agents selected from the group consisting of bis-epoxides, bis-oxazolines and bis-orthoesters.

2. The poly(lactic acid) as defined in claim 1 wherein the average number molecular weight is about 100,000.

3. The poly(lactic acid) as defined in claim 1 wherein said poly(lactic acid) is a self supporting film.

4. The poly(lactic acid) as defined in claim 1 wherein said poly(lactic acid) is a coating on a medical component.

5. The poly (lactic acid) as defined in claim 1 wherein the average number molecular weight is about 25,000–45,000.

6. The poly(lactic acid) as defined in claim 1 further including monomers selected from the group consisting of propylene glycol, ethylene glycol, and bis-hydroxyethyl sulfone.

7. A co-polymer having an average number molecular weight of about 20,000–100,000, comprising:

monomers selected from the group consisting of lactic acid, glycolic acid, and mixtures thereof; and monomers selected from the group consisting of propylene glycol, ethylene glycol, and bis-hydroxyethyl sulfone, said co-polymer coupled one to another by coupling agents selected from the group consisting of bis-epoxides, bis-oxazolines, and bis-orthoesters.

8. The co-polymer as defined in claim 7 wherein said co-polymer is a block polymer of polylactic acid and polyethylene glycol, said co-polymer coupled one to another with a bis-oxazoline coupling agent.

9. The co-polymer defined in claim 8 wherein said co-polymer has an average number molecular weight of about 20,000–45,000.

10. The co-polymer as defined in claim 7 wherein said co-polymer is a condensation product of polylactic acid and an end group modifying reactant selected from the group consisting of a glycol, an epoxide, a dicarboxcylic acid, an acid anhydride, and a thiirane.

12. The copolymer as defined in claim 8 wherein said co-polymer is a coating on a medical component.

11. The co-polymer as defined in claim 8 wherein said co-polymer is a self supporting film.

13. The poly(lactic acid) as defined in claim 1 wherein said poly(lactic acid) is degradable.

* * * * *

UNITED STATES PATENT AND TRADEMARK OFFICE
CERTIFICATE OF CORRECTION

PATENT NO. : 5,470,944
DATED : November 28, 1995
INVENTOR(S) : Patrick V. Bonsignore It is certified that error appears in the above-identified patent and that said Letters Patent is hereby corrected as shown below:

Col. 1, Line 52, omit "hydrolyrically" and insert --hydrolytically--;
Col. 2, Line 4, omit "fastnet" and insert --fastner--;
Col. 5, Line 30, omit "Polyiacticacid" and insert --Polylactic Acid--;
Col. 5, Line 45, omit "." after "System" and insert --,--;
Col. 7, Line 20, omit "R-$\overset{\overset{O}{\|}}{C}$-NH-R' " and insert --R-O-$\overset{\overset{O}{\|}}{C}$-NH-R'--;
Col. 8, Line 38, omit "hydrolyric" and insert --hydrolytic--;
Col. 9, Line 10, omit "--" after second "cellulose" and insert --→--;
Col. 9, Line 35, omit "(EPON 828)" after "O" and insert --(EPON 828)-- below the last "CH$_2$";
Col 10, Line 57, omit "hydrolyric" and insert --hydrolytic--;
Col 11, Line 24, omit "C$_2$O H" and insert --CO$_2$H--.

Signed and Sealed this

Sixteenth Day of July, 1996

*Attest:*

BRUCE LEHMAN

*Attesting Officer*    *Commissioner of Patents and Trademarks*